United States Patent
May

(10) Patent No.: US 9,669,025 B2
(45) Date of Patent: Jun. 6, 2017

(54) USE OF LEVOCETIRIZINE AND MONTELUKAST IN THE TREATMENT OF VASCULITIS

(71) Applicant: INFLAMMATORY RESPONSE RESEARCH, INC., Santa Barbara, CA (US)

(72) Inventor: Bruce Chandler May, Santa Barbara, CA (US)

(73) Assignee: INFLAMMATORY RESPONSE RESEARCH, INC., Santa Barbara, CA (US)

(*) Notice: Subject to any disclaimer, the term of this patent is extended or adjusted under 35 U.S.C. 154(b) by 0 days.

(21) Appl. No.: 14/831,100

(22) Filed: Aug. 20, 2015

(65) Prior Publication Data

US 2015/0352101 A1 Dec. 10, 2015

Related U.S. Application Data

(63) Continuation of application No. PCT/US2014/021732, filed on Mar. 7, 2014.

(60) Provisional application No. 61/780,380, filed on Mar. 13, 2013.

(51) Int. Cl.
| | | |
|---|---|---|
| *A61K 31/495* | (2006.01) | |
| *A61K 31/136* | (2006.01) | |
| *A61K 31/56* | (2006.01) | |
| *A61K 39/395* | (2006.01) | |
| *A61K 31/47* | (2006.01) | |
| *A61K 45/06* | (2006.01) | |
| *A61K 31/496* | (2006.01) | |
| *A61K 31/454* | (2006.01) | |
| *A61K 31/519* | (2006.01) | |
| *A61K 31/573* | (2006.01) | |

(52) U.S. Cl.
CPC .......... *A61K 31/495* (2013.01); *A61K 31/136* (2013.01); *A61K 31/454* (2013.01); *A61K 31/47* (2013.01); *A61K 31/496* (2013.01); *A61K 31/519* (2013.01); *A61K 31/56* (2013.01); *A61K 31/573* (2013.01); *A61K 39/395* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 4,801,612 | A | 1/1989 | Wei et al. |
| 6,384,038 | B1 | 5/2002 | Rubin |
| 6,790,849 | B2 | 9/2004 | Rubin |
| 7,166,640 | B2 | 1/2007 | Berg |
| 7,291,331 | B1 | 11/2007 | Croft et al. |
| 9,044,479 | B2 | 6/2015 | May |
| 2002/0052312 | A1 | 5/2002 | Reiss et al. |
| 2007/0020352 | A1 | 1/2007 | Tripp et al. |
| 2007/0025987 | A1 | 2/2007 | Brunetta |
| 2007/0225285 | A1 | 9/2007 | Hutchinson et al. |
| 2007/0244128 | A1 | 10/2007 | Hutchinson et al. |
| 2008/0260644 | A1 | 10/2008 | Cohen |
| 2012/0040892 | A9 | 2/2012 | Zimmer et al. |
| 2012/0071509 | A1 | 3/2012 | Gore et al. |
| 2013/0011395 | A1 | 1/2013 | Spies et al. |
| 2013/0029949 | A1 | 1/2013 | Hoffmann et al. |
| 2013/0030000 | A1 | 1/2013 | Chobanian et al. |
| 2013/0030009 | A1 | 1/2013 | Harish et al. |
| 2015/0231133 | A1 | 8/2015 | May |
| 2015/0352102 | A1 | 12/2015 | May |
| 2015/0352103 | A1 | 12/2015 | May |
| 2015/0352104 | A1 | 12/2015 | May |
| 2016/0175301 | A1 | 6/2016 | May |

FOREIGN PATENT DOCUMENTS

| | | |
|---|---|---|
| EP | 2520292 A1 | 7/2012 |
| EP | 2 799 071 | 11/2014 |
| JP | 2001-526232 | 12/2001 |
| JP | 2002-511425 | 4/2002 |
| JP | 2011-500847 | 1/2011 |
| KR | 10-2001-0033485 | 4/2001 |
| WO | WO 95/09652 | 4/1995 |
| WO | WO 99/32125 | 7/1999 |
| WO | WO 99/52553 | 10/1999 |
| WO | WO 03/002098 | 1/2003 |
| WO | WO 03/002109 | 1/2003 |
| WO | WO 2006/010283 | 2/2006 |
| WO | WO 2008/100539 | 8/2008 |

(Continued)

OTHER PUBLICATIONS

Kozel et al., Chronic Urticaria Aetiology, Management and Current and Future Treatment Options, 2004, Drugs, 64(22), pp. 2515-2536.*
Muller, B, Urticaria and Angioedema: A practical approach, 2004, American Family Physician, vol. 69, No. 5, pp. 1123-1128.*
Hong et al. Urticaria and Angioedema. Cleveland Clinic Center for Continuing Education, Aug. 2010, pp. 1-15.
International Search Report and Written Opinion for PCT Application No. PCT/US2014/021723, mailed Jun. 26, 2014.
U.S. Appl. No. 14/974,930, filed Dec. 18, 2015, May.

(Continued)

*Primary Examiner* — Kortney L Klinkel
*Assistant Examiner* — Tori M Strong
(74) *Attorney, Agent, or Firm* — Knobbe, Martens, Olson & Bear, LLP

(57) ABSTRACT

The embodiments described herein include methods and formulations for treating vasculitis. The methods and formulations include, but are not limited to, methods and formulations for delivering effective concentrations of levocetirizine and montelukast to a patient in need. The methods and formulations can comprise conventional and/or modified-release elements, providing for drug delivery to the patient.

15 Claims, 2 Drawing Sheets

(56) References Cited

FOREIGN PATENT DOCUMENTS

| WO | WO 2009/022327 | 2/2009 |
|---|---|---|
| WO | WO 2009/055729 | 4/2009 |
| WO | WO 2010/107404 | 9/2010 |
| WO | WO 2011/003074 | 1/2011 |
| WO | WO 2011/041462 | 4/2011 |
| WO | WO 2011/159821 | 12/2011 |
| WO | WO 2012/064301 | 5/2012 |
| WO | WO 2013/012199 | 1/2013 |
| WO | WO 2013/013490 | 1/2013 |
| WO | WO 2013/148366 | 10/2013 |
| WO | WO 2014/164281 | 10/2014 |
| WO | WO 2014/164282 | 10/2014 |
| WO | WO 2014/164285 | 10/2014 |
| WO | WO 2014/164299 | 10/2014 |
| WO | WO 2016/044095 | 3/2016 |

OTHER PUBLICATIONS

Bisgaard Hans, "A Randomized Trial of Montelukast in Respiratory Syncytial Virus Postbronchiolitis", American Journal of Respiratory and Critical Care Medicine, 2003, vol. 167, No. 3, pp. 379-383.
Borish MD, Larry, "Allergic Rhinitis: Systemic Inflammation and Implications for Management", The Journal of Allergy and Clinical Immunology, Dec. 1, 2003, pp. 1021-1031.
Ciebieada, MD et al., "Montelukast with Desloratadine or Levocetirizine for the Treatment of Persistent Allergic Rhinitis", Annals of Allergy, Asthma & Immunology, Nov. 2006, vol. 97, pp. 664-671.
International Preliminary Report on Patentability received in PCT Application No. PCT/US2014/021723, mailed Sep. 24, 2015 in 9 pages.
Khoury, MD et al., "Effect of Montelukast on Bacterial Sinusitis in Allergic Mice", Annals of Allergy, Asthma & Immunology, Sep. 2006, vol. 97, No. 3, pp. 329-335.
Kurowski et al., "Montelukast Plus Cetirizine in the Prophylactic Treatment of Seasonal Allergic Rhinitis: Influence of Clinical Symptoms and Nasal Allergic Inflammation", Allergy, 2004, vol. 59, pp. 280-288.
May, B. Chandler, "A Proposed Model for the Treatment of Acute Inflammation", Mazatlán, Mexico, LXIV Conference of the Mexican College of Clinical Immunology and Allergy, May 29, 2010, pp. 3.
May, B. Chandler, "Contemporary Treatment of Influenza", Santa Barbara, CA, 25th Annual Infectious Disease Conference, Dec. 18, 2009, pp. 36.
Min et al., "Levocetirizine Inhibits Rhinovirus-Induced Bacterial Adhesion to Nasal Epithelial Cells Through Down-Regulation of Cell Adhesion Molecules", Annals of Allergy, Asthma and Immunology, 2012, vol. 108, pp. 44-48.
Moiz et al., "Formulation and Evaluation of Bilayered Tablets of Montelukast and Levocetrizine Dihydrocholoride Using Natural and Synthetic Polymers", International Journal of Drug Delivery 3, Jan. 2011, pp. 597-618.
Parker, MD et al., "A 48 Year Old Man with Recurrent Sinusitis, 1 Year Later", JAMA, Clinical Crossroads Update, Jan. 24/31, 2001, vol. 285, No. 4, p. 462.
Peroni et al., "Combined Cetirizine-Montelukast Preventative Treatment for Food-Dependent Exercise-Induced Anaphylaxis", Annals of Allery, Asthma, & Immunology, Mar. 2010, vol. 104, pp. 272-273.
Schad et al., "Effect of Montelukast on Pro-inflammatory Cytokine Production During Naturally Acquired Viral Upper Respiratory Infections (vURIs) in Adults", Journal of Allergy and Clinical Immunology, Elsevier, Amsterdam, NL, Feb. 2008, vol. 121, No. 2, p. S74.
Tang, Angela, "A Practical Guide to Anaphylaxis", America Family Physician, Oct. 1, 2013, vol. 68, No. 7, pp. 1325-1333.
Tillement et al., "Compared Pharmacological Characteristics in Humans of Racemic Cetirizine and Levocetirizine, Two Histamine $H_1$-Receptor Antagonists", Biochemical Pharmacology, 2003, pp. 1123-1126.
Tillie-Leblond et al., "Relation Between Inflammation and Symptoms in Asthma", Allergy, vol. 64, No. 3, Mar. 1, 2009, pp. 354-367.
Athanasiadis et al., "Urticarial Vasculitis With a Positive Autologous Serum Skin Test: Diagnosis and Successful Therapy", Allergy, 2006, vol. 61, pp. 1484-1485.
Glantschnig et al., "Mass Fraction Profiling Based on X-Ray Tomography and its Application to Characterizing Porous Silica Boules", Applied Optics, Mar. 15, 1987, vol. 26, No. 6, pp. 983-989.
Ingelsson et al., "Nationwide Cohort Study of the Leukotriene Receptor Antagonist Montelukast and Incident or Recurrent Cardiovascular Disease", Journal of Allergy and Clinical Immunology, Mar. 2012, vol. 129, No. 3, pp. 702-707.e2.
Lishchuk-Yakymovych et al., "Positive Correlation Between Serum IL-5 and TNF-alpha Levels and Churg-Strauss Syndrome Activity in Patients Successfully Treated with Motelukast", Journal of Allergy and Clinical Immunology, Entry 295, Feb. 2012, p. 1.
Mansi et al., "ANCA-Associated Small-Vessel Vasculitis", American Family Physician, Apr. 15, 2002, vol. 65, No. 8, pp. 1615-1620.
Nederkoorn et al., "Preventive Antibiotics in Stroke Study: Rationale and Protocol for a Randomised Trial", International Journal of Stroke, Apr. 2011, vol. 6, pp. 159-163.
Taber's® Cyclopedic Medical Dictionary, "Trauma", 18th Edition, 1997, pp. 1988-1989.
Wu et al., "Add-On Therapy with Montelukast in the Treatment of Henoch—Schönlein Purpura", Pediatrics International, 2014, vol. 56, pp. 315-322.
Yu et al., "Montelukast, a Cysteinyl Leukotriene Receptor-1 Antagonist, Dose- and Time-Dependently Protects Against Focal Cerebral Ischemia in Mice", Pharmacology, Jan. 2005, vol. 73, No. 1, pp. 31-40.

* cited by examiner

USE OF LEVOCETIRIZINE AND MONTELUKAST IN THE TREATMENT OF VASCULITIS

CROSS-REFERENCE TO RELATED APPLICATIONS

This application is a continuation of International Application No. PCT/US2014/021723, filed Mar. 7, 2014, which claims the benefit of priority to U.S. Provisional Patent Application No. 61/780,380, filed Mar. 13, 2013. The foregoing applications are fully incorporated herein by reference in their entireties for all purposes.

BACKGROUND

Vasculitis is defined by the presence of inflammatory leucocytes (white blood cells) in the vessel walls with damage to adjacent structures. Loss of vessel integrity can lead to bleeding. Historically, vasculitis was and remains subdivided into three categories which relate to the size of the affected vessel: small vessel, medium vessel, and large vessel. Both arteries and veins are involved. It is generally accepted in the medical community that the exact mechanism of many of the following disorders is yet to be defined. More recently, the presence or absence of an antineutrophil cytoplasmic antibody (ANCA) has refined the classification. Examples of the types of vasculitis are listed in Table VI and are further described below The classic treatment for many of these vasculitides is administration of glucocorticoids, which are often taken for prolonged periods of time. Therapy is dependent upon the nature and extent of the disease process and may include the non-steroidal anti-inflammatory agents, antihistamines, cytotoxic drugs such as cyclophosphamide, or immunosuppressives such as methotrexate. Many of these agents, particularly when taken over extended periods of time, produce significant side effects such as bone marrow suppression (leucopenia, thrombocytopenia), secondary malignancy, sterility, interstitial pulmonary fibrosis, infection, and steroid induced diabetes mellitus which in certain cases are worse that the primary disease itself.

There exists an important unmet need for a therapeutic approach for treating vasculitis and related disorders, including treatment regimens that address one or more of the underlying pathologic mechanisms and/or relieve any of the overt symptoms thereof.

SUMMARY

A method of treating vasculitis in a patient in need thereof is disclosed. The method comprises administering to the patient an effective amount of a combination of levocetirizine and montelukast.

The combination of levocetirizine and montelukast may be administered at the onset of symptoms for any of the disclosed methods.

The combination of levocetirizine and montelukast may be administered in a sequential manner for any of the disclosed methods.

The combination of levocetirizine and montelukast may be administered in a substantially simultaneous manner for any of the disclosed methods.

In some embodiments of the disclosed methods, an additional active agent may be administered. In some embodiments, the active agent is a glucocorticoid, such as prednisone. The additional active agent, in some embodiments, may be a steroidal anti-inflammatory agent. The additional active agent, in some embodiments, may be a non-steroidal anti-inflammatory agent. In some embodiments, the active agent is an antibiotic, such as Augmentin® (amoxicillin/beta clavulanic acid). In some embodiments, the active agent is an antihistamine, such as diphenhydramine (Benadryl®). In some embodiments, the active agent is a cytotoxic agent or an immunosuppressive agent, such as cyclophosphamide, azothiaprine, methotrexate, and mycofenolate mofetil. In some embodiments, the active agent is a monoclonal antibody, such as omalizumab (Xolair®), rituximab, interferon alpha and anti-IL 5 antibodies. Given the intrinsic safety of both levocetirizine and montelukast, the combination may be used with almost any of the aforementioned agents. Therapy may be primary or secondary, and if secondary, administered to supplement existing treatment to effect the desired response. Once achieved, (reduction in symptoms/improvement in associated laboratory values) the more toxic, former therapy(ies) may be tapered and in select cases, completely discontinued. The combination of levocetirizine plus montelukast may continue until the defined laboratory or clinical endpoint(s) traditionally acknowledged in the literature for that specific type of vasculitis has (have) been reached.

In some embodiments of the disclosed methods, the combination may be administered to the patient by one or more of the routes consisting of enteral, intravenous, intraperitoneal, inhalation, intramuscular, subcutaneous and oral.

In some embodiments, the levocetirizine and montelukast may be administered by the same route.

One embodiment is directed to methods, formulations and kits for treating vasculitis. The methods and formulations include, but are not limited to, methods and formulations for delivering effective concentrations of levocetirizine and montelukast to a patient in need. The methods and formulations can comprise conventional and/or modified-release elements, providing for drug delivery to the patient.

In some embodiments, the methods of treatment, formulations and kits may include e.g., a bilayer tablet, comprising levocetirizine and montelukast in separate layers, for daily administration. Alternatively, each medication may be administered separately (one tablet of levocetirizine and one tablet of montelukast per day in the evening). In some embodiments, a combination of levocetirizine and montelukast, either as a single formulation or as separate formulations, may be administered for 1, 2, 3, 4, 5, 6, 7, 8, 9, 10, 11, 12, 13, 14, or 15 days for the treatment of vasculitis. The bilayer tablets or the separate tablets may be packaged in a blister pack supplied for a 7 to 10 day course of therapy, with instructions including indications, administration instructions and precautions. The bilayer tablets or the separate tablets may be packaged in a blister pack supplied for a 30 day course of therapy, with instructions including indications, administration instructions and precautions. In some embodiments, a combination of levocetirizine and montelukast, either as a single formulation or as separate formulations, may be administered for at least once daily for up to several weeks, months, or years. In some embodiments, a combination of levocetirizine and montelukast, either as a single formulation or as separate formulations, may be administered for as long as needed to control symptoms of vasculitis. In some embodiments, a combination of levocetirizine and montelukast, either as a single formulation or as separate formulations, may be administered daily or twice daily dosing until necessary to suppress inflammation.

In some embodiments, the combination of levocetirizine and montelukast may be administered, as single formulations or as separate formulations as follows: 5-15 mg per day in divided doses twice a day of levocetirizine and 10-20 mg per day in divided doses twice a day of montelukast.

DETAILED DESCRIPTION

Figure 1:
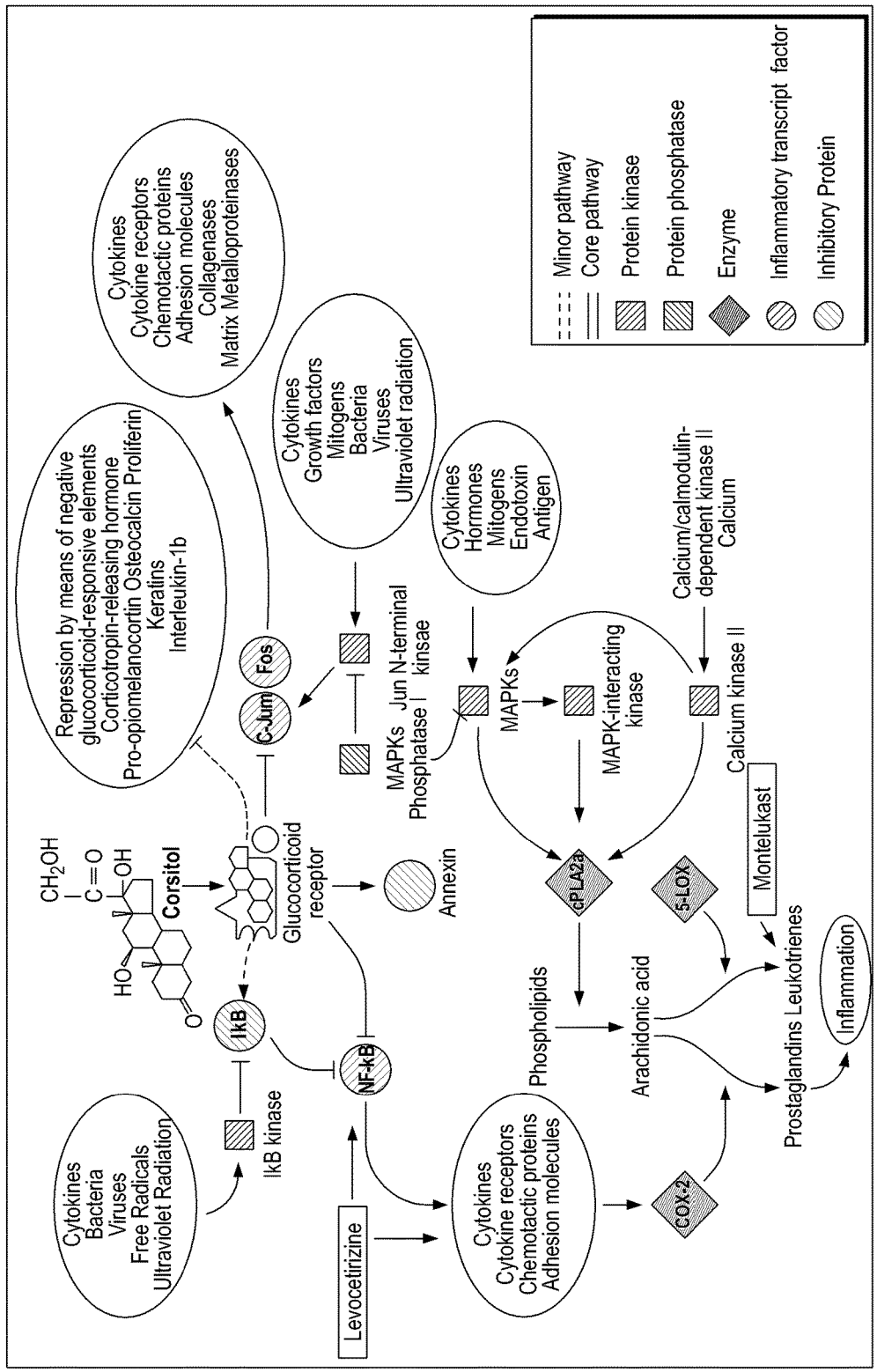
FIG. 1 shows a diagram of the proposed anti-inflammatory mechanism of action of levocetirizine and montelukast utilizing a steroid model pathway.

The present embodiments relate to the combination of levocetirizine and montelukast as a medicament for the treatment of vasculitis. Administration of levocetirizine and montelukast in combination exhibits synergistic effects and unexpectedly superior results in the treatment of vasculitis. Moreover, combinations of levocetirizine and montelukast can be used safely in conjunction with many existing treatment protocols.

Levocetirizine is an antihistamine and montelukast is a leukotriene receptor antagonist. As described herein, synergy between levocetirizine and montelukast shortens the course of the disease processes, thereby decreasing morbidity and mortality. This combined therapy also can improve quality of life from the amelioration of symptoms/side effects/disease process itself and can decrease health-care costs. This synergistic effect can be observed in the use of a combination of levocetirizine and montelukast to treat non-IgE-mediated inflammation and combined non-IgE-mediated and IgE-mediated inflammation. Not wishing to be bound by a particular theory, the non-IgE-mediated response may be related, at least in part, to the fact that both levocetirizine and montelukast affect eosinophil migration, the leukocyte that is considered a hallmark of inflammation.

Levocetirizine, a potent H1-antihistamine, acts primarily by down-regulating the H1 receptor on the surface of mast cells and basophils to block the IgE-mediated release of histamine which cause the cardinal symptoms of allergic rhinitis: sneezing, rhinorrhea, nasal congestion, itchy palate and itchy red and watery eyes. Levocetirizine offers a short time to peak plasma level, 0.9 hr., a short time to steady state level, 40 hours, a low volume of distribution, 0.4 L/kg, and an enhanced receptor affinity of 5× over first generation mepyramine in an acidic pH (many acute inflammatory disease states are associated with acidosis, a low physiologic pH). Levocetirizine has a 24 hour receptor occupancy of ~75%, the highest of the commercially available antihistamines. Receptor occupancy of the second generation antihistamines appears to correlate with the pharmacodynamic activity in skin wheal and flare studies and with efficacy in allergen challenge chamber studies. Levocetirizine is approved in the US for the treatment of perennial allergic rhinitis and chronic idiopathic urticaria down to six months of age.

Levocetirizine has been objectively established as the most potent of the five modern generation antihistamines through histamine induced wheal and flare data. For example, levocetirizine at 5 mg per day is more effective than fexofenadine at its commonly prescribed dose of 180 mg per day in the United States. In Europe the adult dose is 120 mg per day. Levocetirizine has a lower volume of distribution, greater histamine receptor affinity in an inflamed state (low pH), and greater receptor occupancy at 24 hours at physiologic doses than fexofenadine. The corresponding values are shown in Table I.

TABLE I

COMPARISON BETWEEN FEXOFENADINE AND LEVOCETIRIZINE

| | Fexofenadine | Levocetirizine |
| --- | --- | --- |
| Vd-L/kg | 5.6 L/kg | 0.4 L/kg |
| Receptor affinity in an acidic ph | increased 2x | increased 5x |
| Histamine receptor occupancy at 24 hours | ~25% | ~75% |
| Steady-state level | 3 days | 40 hours |

Levocetirizine decreases human rhinovirus titers in vitro by log-2. Not to be bound by a particular theory, the cellular mechanism of action is a proposed reduction of the activation of the intracellular protein complex NF-kB (nuclear factor kappa B) which is in turn responsible for the reduction of I-CAM-1. I-CAM-1, a transmembrane protein, is viewed as the portal of entry of human rhinovirus into the cell. Rhinovirus can be found in ~50% of cases of acute asthma and is responsible for 30-50% cases of the 'common cold.' A one-log reduction in viral titers has been independently determined to correlate with improved symptoms. In addition, levocetirizine has been shown to decrease eosinophil migration and decrease inflammatory mediators, IL-4, IL-6, and IL-8. IL-6, a signaling protein, regulates in part: fever, the body's response to trauma, and the acute (immediate) phase of the allergic reaction.

Montelukast, a leukotriene receptor antagonist, acts by binding with high affinity and selectivity to the CysLT1 receptor to inhibit the physiologic actions of the leukotriene LTD4. Leukotrienes are fatty signaling molecules whose effects include airway edema, smooth muscle contraction and altered cellular activity associated with the inflammatory process. Overproduction of leukotriene is a major cause of inflammation in asthma and allergic rhinitis. The cysteinyl leukotrienes (LTC4, LTD4, LDE4) are products of arachidonic acid metabolism. These leukotrienes are released from various cells including mast cells and eosinophils. They bind to receptors in the human airway and on other pro-inflammatory cells including eosinophils and certain myeloid stem cells. The cysteinyl leukotrienes have been correlated with the pathophysiology of asthma and allergic rhinitis.

Leukotriene $D_4$ is the most potent of the cysteinyl leukotrienes in contracting airway smooth muscle. Leukotriene receptors, such as $CysLT_1$, are found throughout the cells of the respiratory tree (including airway smooth muscle cells and airway macrophages) as well as on other pro-inflammatory cells in the body, particularly eosinophils and certain myeloid stem cells. Leukotrienes also function to promote the recruitment of eosinophils, dendritic cells and T cells. Eosinophil infiltration is considered by some authorities as a hallmark of inflammation.

Montelukast is FDA approved in the US for the treatment of perennial allergic rhinitis, asthma, seasonal allergic rhinitis, and exercised induced bronchospasm. Montelukast has been shown to be ineffective in improving asthma control or cold symptom scores caused by experimental rhinovirus infection. See Kloepfer K M, et al., Effects of montelukast in patients with asthma after experimental inoculation with human rhinovirus 16. Annals Allergy Asthma Immunology. 2011; 106:252-257. Unlike levocetirizine, no decrease in viral shedding was observed in rhinovirus-infected individuals treated with montelukast and there was no significant difference in reported cold symptom scores compared to placebo-treated individuals. Analysis of secondary outcomes suggests that montelukast may protect against reductions in lung function and increases in sputum eosinophils caused by common cold infections. During the recovery phase the percentage of sputum eosinophils was elevated in the placebo group, while the montelukast group remained at baseline levels. Further, peak expiratory flow was not decreased in the montelukast-treated patients. Other studies have shown that montelukast treatment has no effect on the respiratory symptoms of patients with acute respiratory syncitial virus bronchiolitis. See Bisgaard, H., et al., Study of montelukast for the treatment of respiratory symptoms of post-respiratory syncitial virus bronchiolitis in children, Am. J. Respir. Crit. Care Med., 2008; 178:854-860; and Proesmans, M., et al., Montelukast does not prevent reactive airway disease in young children hospitalized for RSV bronchiolitis, Acta Paediatr. 2009; 98:1830-34. However, some studies indicate that treatment with montelukast reduced the number of days with worsened asthma symptoms and unscheduled doctor's visits in children with mild allergic asthma and resulted in a modest reduction of symptoms in children with recurrent wheezing when given at the first sign of upper respiratory tract illness. See Sears, M. R. and Johnston, N. W., Understanding the September asthma epidemic. J. Allergy Clin. Immunol. 2007; 120:526-29; Bacharier, L. B., et al., Episodic use of an inhaled corticosteroid or leukotriene receptor antagonist in preschool children with moderate-to-severe intermittent wheezing. J. Allergy Clin. Immunol. 2008; 122:1127-35.

Montelukast reaches a steady state level, like the second generation antihistamine, levocetirizine, in less than two days. Unlike other currently available leukotriene modulators, zileuton and zafirlukast, routine monitoring of liver function tests is not required. There are no drug interactions with warfarin, theophylline, digoxin, terfenadine, oral contraceptives, or prednisone.

The two molecules are safe, i.e., FDA approved in the United States for allergic disorders down to age six months. They can be given primarily or in conjunction with many of the existing therapeutic protocols for the treatment of inflammation, including but not limited to, influenza, acute asthma and the common cold. Both medications are pregnancy category B (Table II).

Existing treatment of inflammation focuses on the underlying condition and nature of the presentation. Commonly employed are a myriad of agents such as: diphenhydramine (Benadryl®), oxygen, epinephrine, steroids, beta-agonists, non-steroidal anti-inflammatory agents (NSAIDS), antipyretics, antibiotics, antifungals, and antivirals. Paradoxically, the commonly employed NSAIDS actually increase the production of leukotrienes.

Steroids, which are widely used to treat inflammation, have significant short and long-term side-effects (Table III). With regard to treating inflammation associated with rhinosinusitis, nasal steroids have their limitations, particularly in the elderly and those patients on aspirin, clopidogrel or warfarin prescribed to reduce the risk of stroke and heart attack. Even in patients who do not take these traditional "blood thinners," the risk of spontaneous epistaxis from nasal steroid sprays is between 4-22%. The risk of epistaxis is medication dependent. Epistaxis is a significant consideration in many patients 55 or older.

TABLE III

| STEROID SIDE EFFECTS | |
| --- | --- |
| Short term | Long term |
| Increased propensity for opportunistic infection | Glaucoma |
| | Cataracts |
| Increased blood pressure | High-blood pressure |
| Mood changes | Heart disease |
| Increased blood sugar | Diabetes mellitus |
| Increased intraocular pressure | Obesity |
| Water retention | Acid reflux/GERD |
| Weight gain | Osteoporosis |
| Increased risk for congestive heart failure | Myopathy |
| Flushing | Increased propensity for opportunistic infection |
| Increased appetite | |
| Insomnia | Cushing syndrome |

The typical daily dosage for levocetirizine is 5 mg for adults, and levocetirizine exhibits the following advantageous properties: i) Short time to reach peak plasma levels—0.9 hr; ii) Short time to steady state level—40 hrs; iii) Low volume of distribution (goes directly to the target receptor); iv) High receptor occupancy at 24 hours ~75%; v) Increased receptor affinity in inflamed tissue (acidic pH; up to 5× that of first generation molecules); vi) Pregnancy category B; vii) FDA approved down to six months for other disease states,

TABLE II

| PREGNANCY CATEGORY DEFINITIONS | | |
| --- | --- | --- |
| Category | Definition | Explanation |
| A | Generally acceptable | Controlled studies in pregnant women show no evidence of fetal risk. |
| B | May be acceptable | Either animal studies show no risk but human studies not available or animal showed minor risks and human studies were done and showed no risk. |
| C | Use with caution if benefits outweigh risks | Animal studies show risk and human studies not available or neither animal nor human studies were done. |
| D | Use in life-threatening emergencies when no safer drug is available | Positive evidence of human fetal risk. |
| X | Do not use in pregnancy | Risks involved outweigh potential benefits. Safer alternatives exist. | i.e., perennial allergic rhinitis and chronic idiopathic urticaria; viii) Anti-inflammatory properties; and ix) Anti-viral properties. Studies in humans have shown that doses of levocetirizine up to 30 mg/day can be safely administered.

Montelukast, a leukotriene receptor antagonist, acts concurrently to protect the respiratory tree as well as block mediators in the inflammatory cascade. The typical daily dosage of montelukast is 10 mg for adults, and montelukast exhibits the following advantageous properties: i) montelukast is a selective receptor antagonist, inhibiting the physiologic action of $LTD_4$ at the $CysLT_1$ receptor; ii) montelukast binds with high affinity and selectivity to the $CysLT_1$ receptor without producing any agonist activity; iii) montelukast is rapidly absorbed; iv) montelukast reaches a peak plasma concentration in 3-4 hours; v) the oral bioavailability and $C_{max}$ of montelukast are not affected by a standard meal; vi) montelukast has a linear pharmacokinetics to 50 mg; vii) doses as low as 5 mg in adults cause substantial blockage of $LTD_4$-induced bronchoconstriction; viii) in a placebo controlled crossover study, montelukast inhibited early-phase bronchoconstriction due to antigen challenge by 75%; ix) montelukast is FDA approved down to six months of age; and x) montelukast has no drug interactions with warfarin, theophylline, digoxin, terfenadine, oral contraceptives, or prednisone. Montelukast has been administered at doses up to 200 mg/day to adult patients for 22 weeks and in short-term studies, and up to 900 mg/day to patients for approximately one week without clinically important adverse experiences.

Accordingly, both levocetirizine and montelukast are pregnancy category B in the United States and are FDA approved in the United States down to six months of age for other disease processes. Moreover, both drugs have only once daily dosing, and no routine monitoring of blood work is necessary for most clinical situations. Further, both drugs exhibit minimal clinically relevant interactions with other medications. As described herein, both levocetirizine and montelukast administered orally reach steady state levels within two days to rapidly produce a synergistic and complementary anti-inflammatory effect.

Administration of montelukast and a second generation antihistamine, fexofenadine, has a synergistic effect in the treatment of allergic rhinitis. Allergic rhinitis, also known as pollenosis or hay fever, is an allergic inflammation of the nasal airways which occurs when an allergen such as pollen or dust is inhaled by an individual with a genetically susceptible immune system (estimated at >20 percent of the population). The allergen triggers antibody production, a serum specific immunoglobulin E (IgE), which in turn can bind to mast cells and basophils containing histamine. Upon re-exposure to the offending antigen, histamine is released causing the itching, swelling, and mucus production which are well known to seasonal allergy suffers. A combination of montelukast and fexofenadine reduced nasal congestion both subjectively, using patient diary and VAS evaluations, and objectively, using rhinomanometry and physical examination, with statistical significance compared to fexofenadine alone or fexofenadine with placebo.

However, the scientific literature does not clearly indicate whether the combination of an antihistamine plus a leukotriene offers an advantage over each alone for treatment in general. For example, in one chronic inflammatory disease state, chronic idiopathic urticaria, montelukast did not appear to offer an advantage over the second generation antihistamine desloratadine. See DiLorenzo G, et. al. Randomized placebo-controlled trial comparing desloratadine and montelukast in combined therapy for chronic idiopathic urticaria. J Allergy Clin Immunol 2004; 114-:619-25. Further, the FDA in April 2008 did approve the combination of loratadine, also a second generation antihistamine, and montelukast for the treatment of allergic rhinitis and asthma, finding no benefit from a combined pill.

Here, we describe the unexpected synergistic effects of combining levocetirizine and montelukast. Not wishing to be bound by a particular theory, a detailed examination of the pharmacokinetics of levocetirizine at the cell level illuminates the unique inflammatory properties that extend beyond the IgE mediated release of histamine. Levocetirizine exhibits a low volume of distribution (0.4 L/kg), prolonged dissolution time from the H1 receptor in an acidic pH, enhanced receptor affinity as a pure isomer of cetirizine, and the highest receptor occupancy at 24 hours of any currently available antihistamine. Such parameters impart an inflammatory effect by down regulating IL-4, IL-6, IL-8 as well as cellular adhesion molecules. The latter are a homogeneous group of inducible immunoglobulins, integrins and selectins involved in cell-to-cell adhesion, cellular recruitment, homing and healing. In addition levocetirizine has been shown in vivo to decrease ICAM-1, IL-6, IL-8, TLR3 expression and NF-kappa B activation resulting in decreased human rhinovirus titers by log-2. Many rhinovirus serotypes share the same cellular receptor identifying ICAM-1 as the portal of entry into the cell. Levocetirizine inhibits rhinovirus-induced ICAM-1 and cytokine expression and viral replication in airway epithelial cells. One log reduction in viral shedding results in a significant clinical benefit in HRV-infected (human rhinovirus) patients.

An unmet clinical need arose in 2009 with the H1N1 pandemic. The primary drug of choice for influenza, oseltamivir, did not appear to reduce influenza related lower respiratory tract complications. For neuraminidase inhibitors, there was a shortening of the illness by only one half to one day, which indicated that neuraminidase inhibitors do not prevent infection or stop nasal viral excretion, and therefore may be a suboptimal means of interrupting viral spread in a pandemic. Moreover, during this time frame, California reported alarming data on the severity of H1N1 influenza in pregnant and postpartum women, i.e., from Apr. 23 through Aug. 11, 2009 22% of pregnant or postpartum women required intensive care for the treatment of H1N1 and 8% died. Clinically it was demonstrated that the combination of levocetirizine plus montelukast (the latter added to protect the lower airway; both of which were Pregnancy Category B), could be safely and effectively used to ameliorate/shorten the course of influenza.

Not wishing to be bound by a particular theory, the steroid model suggests that levocetirizine acts in a non-IgE-mediated capacity at the level of NF-kB (See FIG. 1) whereas montelukast acts at the CysLT1 receptor to inhibit the physiologic actions of LTD4. Both molecules are known to reduce the quantity of eosinophils or their migration to site of inflammation. Montelukast, in addition, also decreases the recruitment of dendritic cells and T cells.

The actions of levocetirizine plus montelukast surpass the individual physiologic mechanisms of each, well beyond the treatment of allergic rhinitis and asthma. At least in part, it is the anti-viral and anti-inflammatory properties of levocetirizine vis-a-vis nuclear factor kB; the inhibition of the actions of LTD4 by montelukast, underscored by ability of both levocetirizine and montelukast to inhibit the eosinophil quantity/migration, which impart synergy. This synergy is reflected by significantly improved clinical outcomes in a myriad of acute and chronic inflammatory disease states.

Embodiments described herein relate to methods of treating inflammation of the entire respiratory tree, including in part, the nose and paranasal sinuses known as rhinosinusitis with montelukast and levocetirizine. Rhinosinusitis considered on a timeline may be acute, with a duration of less than six weeks (usually 4-6 weeks), subacute, having a duration of six to twelve weeks, or chronic, having a duration of greater than or equal to twelve weeks. Acute rhinosinusitis may be precipitated by multiple factors not limited to chemical irritation, trauma, allergic rhinitis or an earlier upper respiratory tract infection, which may be bacterial, viral, or, less commonly, fungal in origin. The most common causative agents of acute sinusitis of bacterial origin are *Streptococcus pneumoniae, Haemophilus influenzae, Moraxella catarrhalis, Staphylococcus aureus*, other streptococci species, anaerobic bacteria, and, less commonly, gram negative bacteria. Bacterial sinusitis tends to be more persistent than viral rhinosinusitis, i.e., the common cold, which typically lasts for 7 to 10 days.

Several embodiments described herein relate to the treatment of acute rhinosinusitis caused by a viral or bacterial infection with montelukast and levocetirizine. In some embodiments, montelukast and levocetirizine are taken prophylactically to prevent a viral respiratory tract infection from escalating to an acute, often opportunistic, secondary bacterial sinusitis, bronchitis and/or pneumonia. In some embodiments, montelukast and levocetirizine are administered immediately, one hour, 6 hours, 12 hours, 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, and/or 30 days after exposure to the pathogens (virus, bacteria, fungi, etc.). Several embodiments relate to the treatment of patients with clinical manifestations of influenza with montelukast and levocetirizine. In some embodiments, montelukast and levocetirizine treatment reduces the duration of influenza. In some embodiments, montelukast and levocetirizine treatment reduces the severity of influenza symptoms. Several embodiments relate to the treatment of patients with clinical manifestations of the common cold with montelukast and levocetirizine. In some embodiments, montelukast and levocetirizine treatment reduces the duration of the cold. In some embodiments, montelukast and levocetirizine treatment reduces the severity of cold symptoms.

Chronic rhinosinusitis is an inflammatory condition/disease of the nose and paranasal sinuses lasting for greater than or equal to twelve weeks. Symptoms include in part, any combination of nasal congestion, facial pain, headache, coughing, an increase in asthma symptoms, malaise, discharge, feeling of facial tightness, dizziness, and/or aching teeth. Rhinosinusitis in general can be categorized into four categories: (1) acute bacterial rhinosinusitis (ABRS), (2) chronic rhinosinusitis without nasal polyposis (CRSsNP), (3) chronic sinusitis with nasal polyposis (CRSwNP), and (4) allergic fungal rhinosinusitis (AFRS). See Meltzer, EO. Rhinosinusitis: Developing guidance for clinical trials. J Allergy Clin Immunol 2006 November; S20. Nasal polyposis is a subgroup of chronic rhinosinusitis in which the inflammation of the nose is associated with two or more of the following signs and symptoms: nasal obstruction or congestion, nasal discharge, hyposmia or anosmia, facial pain or feeling of pressure, endoscopic evidence of polyps or mucopurulent discharge from middle meatus with or without edema or mucosal obstruction of the meatus and CT images which show mucosal changes of osteomeatal complex or paranasal sinuses. See Fokkens W, et. al. EAACI position paper on rhinosinusitis and nasal polyps executive summary. Allergy, 2005; 60, 583-601., Fokkens, W, et. al. European Position Paper on Rhinosinusitis and Nasal Polyps group (2007) European position paper on rhinosinusitis and nasal polyps. Rhinology 2007; 20,1-136. Conventional treatment for chronic rhinosinusitis often involves functional endoscopic sinus surgery, antibiotics, systemic and topical steroids, and to a much lesser extent an antihistamine or leukotriene modulator. The use of antihistamines in patients with only polyps has not been extensively studied. See Casale M, et. al. Nasal Polyposis: From Pathogenesis to Treatment, an Update. Inflammation & Allergy—Drug Targets 2011, 10, 158-163. Mometasone furoate monohydrate, a topical nasal steroid spray, is the only FDA approved medication in the United States for the treatment of nasal polyposis. The recommended dose is two squirts each nostril twice a day.

Embodiments described herein relate to the treatment of chronic rhinosinusitis with montelukast and levocetirizine. Several embodiments described herein relate to the treatment of nasal polyposis with montelukast and levocetirizine. In some embodiments, montelukast and levocetirizine treatment reduces the size and/or number of polyps. Some embodiments relate to the treatment of chronic rhinosinusitis with montelukast and levocetirizine in the absence of steroids, antibiotics or surgical treatment. In other embodiments, montelukast and levocetirizine are administered in conjunction with antibiotics and/or steroids and/or surgical treatment as deemed clinically applicable. The chronic rhinosinusitis treatment protocol with or without other treatment modalities is as follows:

TABLE IV

TREATMENT PROTOCOL FOR CHRONIC RHINOSINUSITIS

| Levocetirizine - US | |
|---|---|
| Adults: | 5 mg/day |
| Children: 6-11 years of age: | 2.5 mg/day |
| Children: 6 months to 5 years: | 1.25 mg/day |
| Montelukast - US | |
| Adults: | 10 mg orally/day |
| Children 6-14 years of age: | 5 mg orally/day |
| Children 6 months-5 years of age: | 4 mg orally/day |

Patients may be seen at least quarterly in the office with endoscopic review of the nose/paranasal sinuses when clinically appropriate. A pretreatment and follow-up CT scan of the perinasal sinuses at 6 months to one year post initiation of therapy may be performed to provide objective data on which to tailor existing medical therapy.

Several embodiments relate to a method of treating rhinitis with montelukast and levocetirizine. Rhinitis, inflammation of the nasal passages, is commonly caused by a viral or bacterial infection, including the common cold, the latter of which is caused primarily by Rhinoviruses and Coronaviruses. See Eccles R. Understanding the Symptoms of the Common Cold and Influenza. Lancet Infectious Diseases 2005; 5(11): 718-725. Rhinitis is categorized as: (i) infective rhinitis; (ii) nonallergic rhinitis; and (iii) allergic rhinitis. Several embodiments relate to a method of treating infective rhinitis with montelukast and levocetirizine. Some embodiments relate to a method of treating nonallergic rhinitis with montelukast and levocetirizine. Some embodiments relate to a method of treating allergic rhinitis with montelukast and levocetirizine.

Several embodiments described herein relate to the treatment of chronic rhinosinusitis with montelukast and levocetirizine. Some embodiments, relate to the treatment of chronic rhinosinusitis with montelukast and levocetirizine in the absence of steroid or antibiotic treatment. In other embodiments, montelukast and levocetirizine are administered in conjunction with antibiotics and/or steroids.

Several embodiments relate to a method of treating non-IgE-based inflammation with montelukast and levocetirizine.

Several embodiments relate to a method of treating combined IgE and non-IgE-mediated inflammation with montelukast and levocetirizine.

The following Table V shows the existing country guidelines for dosages in the treatment of allergic disorders.

TABLE V

GUIDELINES FOR DOSAGES IN THE TREATMENT OF ALLERGIC DISORDERS

| Levocetirizine - US | |
|---|---|
| Adults: | 5 mg/day |
| Children: 6-11 years of age: | 2.5 mg/day |
| Children: 6 months to 5 years: | 1.25 mg/day |
| Montelukast - US | |
| Adults: | 10 mg orally/day |
| Children 6-14 years of age: | 5 mg orally/day |
| Children 6 months-5 years of age: | 4 mg orally/day |

Several embodiments relate to the use of a combination of levocetirizine and montelukast to treat a bacterial infection. Examples of bacterial infections that may be treated by a combination of levocetirizine and montelukast include, but are not limited to, acute bacterial rhinosinusitis (ABRS). In some embodiments, levocetirizine and montelukast may be administered with an antibiotic as determined by local presentation.

Several embodiments relate to the use of a combination of levocetirizine and montelukast to treat otitis media with effusion and associated ear disorders such as chronic mastoiditis and eustachian tube dysfunction (the auditory tube leading from the back of the nose to the middle ear). In some embodiments, levocetirizine and montelukast may be administered with antibiotics to treat for example, acute otitis media with purulent middle ear effusion. In some embodiments, levocetirizine and montelukast may be administered without antibiotics to treat chronic middle ear effusion, for example, chronic otitis media. In some embodiments, levocetirizine and montelukast may be administered with other treatment modalities such as, but not limited to, steroids and/or antiviral agents.

Several embodiments relate to the use of a combination of levocetirizine and montelukast to treat allergic fungal rhinosinusitis (AFRS). In some embodiments, levocetirizine and montelukast may be administered with other treatment modalities such as, but not limited to, steroids and/or an antifungal agent.

Intravenous therapy of levocetirizine and montelukast, the latter currently under investigation in the United States, would enhance the individual and combined clinical response presently seen with the administration of oral medication. The IV montelukast plasma concentration area under the curve profile, 7 mg, is comparable to the approved 10 mg oral montelukast tablet. The former has been shown in acute asthmatics to significantly improve FEV1 (forced expiratory volume at one sec) at 10 minutes when compared with placebo.

Accordingly, the dosing for acute inflammation could be daily as delineated above individually in the same setting, as a dual-layer tablet(s), and/or as a blister pack containing both medications for a 10 day course of therapy. For a moderate to severe clinical presentation, the levocetirizine component can be given at time zero (5 mg), 12 hours (5 mg) and 24 hours (5 mg), during the first 24 hour day, in order to achieve a steady state level of the molecule in less than 40 hours. Levocetirizine human dosing safety studies have been performed at up to 30 mg/day. Sedation is the principal side effect experienced at higher doses. Independent research has shown that levocetirizine alone can be dosed at 20 mg/day to treat severe cases of idiopathic urticaria.

The application for the combination of levocetirizine and montelukast includes, but is not limited to treating, ameliorating, or preventing the following symptoms. For Influenza, the combination can be useful to shorten the course of seasonal flu and prevent or minimize the development of lower respiratory tract infections/complications, and/or to establish an improved, safe, world-wide protocol for influenza prior to the next pandemic, e.g., H5N1 with its associated 50% mortality rate. For upper respiratory tract infections, not limited to rhinovirus, the combination can be useful to limit the infection itself, and/or to prevent or reduce the potential development of secondary sinusitis, bronchitis and pneumonia. The combination can be useful for treatment of Ebstein-Barr Virus, particularly, but not limited to those patients with respiratory involvement.

For acute asthma in conjunction with existing protocols, not limited to exacerbations caused by rhinovirus (~50% of cases), the combination can be useful to shorten the course of the event, reduce hospitalizations and death. The combination can be useful for pre-treatment of patients allergic to one or more classes of antibiotics requiring antimicrobial therapy. These patients are at risk, 4-10× over the general population, of developing a subsequent ALE (allergic-like event). For patients with moderate to severe life-threatening disease requiring dual/triple antibiotics, the combination can be useful to reduce the probability of developing a side-effect(s) from the primary treatment medications. The combination can be useful during and following radiation therapy to ameliorate the inflammatory response. The combination can be useful for patients requiring steroids for the treatment of inflammation who are otherwise at increased risk for the development of steroid induced complications. Examples include but are not limited to the following: i) A severe insulin dependent diabetic with an infection such as facial paralysis, and ii) Patient with latent Tuberculosis. For patients on antiviral medication for acute disease, the combination can be used to prevent complications related to the medication(s) as well as complications associated with the disease process itself. The combination can be used to treat serum sickness, with or without steroids. For pre-treatment of patients on immunotherapy, the combination can be used to prevent or ameliorate the risk of a systemic reaction. Examples of high risk patients with the potential to develop a life-threatening, systemic event include but are not limited to severe asthmatics, those patients with a concurrent respiratory tract infection, and those patients with a prior history of a systemic reaction. For pre and intra-treatment of those patients on chemotherapy, the combination can be used to ameliorate side effects associated with the administration of chemotherapeutic drug(s). For patients exhibiting a transfusion reaction, the combination can be used to limit the side effects/life threatening event during the initial reaction and in preparation for any requisite subsequent transfusion.

As will be readily apparent to one skilled in the art, the useful in vivo dosage of levocetirizine and montelukast to be administered and the particular mode of administration will vary depending upon the age, weight, medical condition of the patient, the severity of the condition to be treated, the route of administration, the renal and hepatic function of the patient, and mammalian species treated, the particular compounds employed, and the specific use for which these compounds are employed. The determination of effective dosage levels, that is the dosage levels necessary to achieve the desired result, can be accomplished by one skilled in the art using routine pharmacological methods. Typically, human clinical applications of products are commenced at lower dosage levels, with dosage level being increased until the desired effect is achieved. Advantageously, compounds of the present embodiments may be administered, for example, in a single daily dose, or the total daily dosage may be administered in divided doses of two, three or four times daily.

TABLE VI

TREATMENT PROTOCOL FOR ACUTE INFLAMMATION NOT LIMITED TO INFLUENZA AND THE COMMON COLD

Levocetirizine - US

| | |
|---|---|
| Adults: | 5 mg/day |
| Children: 6-11 years of age: | 2.5 mg/day |
| Children: 6 months to 5 years: | 1.25 mg/day |

Montelukast - US

| | |
|---|---|
| Adults: | 10 mg orally/day |
| Children 6-14 years of age: | 5 mg orally/day |
| Children 6 months-5 years of age: | 4 mg orally/day |

Depending upon the severity of the acute process, the doses in Table VI can be modified. For example, the age appropriate dose for levocetirizine may be given at time zero (at presentation) with an additional age appropriate dose at 12 hours. In order to protect the lower airway, particularly in the face of bronchitis/pneumonia, a dose of montelukast may be given at time zero (at presentation) with an additional age appropriate dose of montelukast at 12 hours. In this fashion the steady state level of the two drugs would approach 24 hours. Montelukast, like levocetirizine, is considered a very safe molecule. Montelukast has been administered at doses up to 200 mg/day (20× the standard adult daily dose) to adult patients for 22 weeks and in short-term studies, up to 900 mg/day (90× the standard adult daily dose) to patients for approximately one week without clinically important adverse events. Dosing duration may parallel the generally accepted protocols for their respective disease states. For example, conventional therapy for an acute infectious disease process is typically administered for 5-14 days. A course of combined levocetirizine once daily plus montelukast once daily may be given for the same duration. For the treatment of chronic inflammatory disease states, an age appropriate once daily dosing of each medication may also be administered.

Vasculitis

Several embodiments relate to the use of a combination of levocetirizine and montelukast for the treatment of vasculitis. Several embodiments disclosed herein relate to the use of a combination of levocetirizine and montelukast for the treatment of small vessel vasculitis, medium vessel vasculitis, and large vessel vasculitis. In some embodiments, the combination of levocetirizine and montelukast is used for the treatment of antineutrophil cytoplastmic antibodies-associated vasculitis. In some embodiments, the combination of levocetirizine and montelukast is used for the treatment of non-antineutrophil cytoplastmic antibodies-associated vasculitis.

Vasculitis is defined by the presence of inflammatory leucocytes (white blood cells) in the vessel walls with damage to adjacent structures. Both arteries and veins are involved. Loss of vessel integrity can lead to bleeding. Historically, vasculitis was and remains subdivided into three categories which relate to the size of the affected vessel: small vessel, medium vessel, and large vessel. It is generally accepted in the medical community that the exact mechanism of many of the disorders listed in Table VI is yet to be defined.

TABLE VI

CLASSIFICATION OF VASCULITIS BY VESSEL SIZE

| | |
|---|---|
| Small Vessel: | Behçet's syndrome |
| | Churg-Strauss syndrome |
| | cutaneous vasculitis |
| | Henoch-Schönlein purpura, |
| | Microscopic polyangiitis |
| | Wegener's granulomatosis |
| | cryoglobulinemic vasculitis, |
| | hypersensitivity vasculitis, |
| | vasculitis secondary to connective tissue disorders |
| | vasculitis secondary to viral infections |
| Medium Vessel | Thromboangiitis obliterans (small and medium vessel) |
| | Cutaneous vasculitis (small and medium vessel) |
| | Kawasaki disease |
| | Polyarteritis nodosa (small and medium vessel) |
| | primary central nervous system vasculitis |
| Large Vessel | Polymyalgia rheumatica |
| | Takayasu's arteritis |
| | Temporal (giant cell) arteritis |

Small vessel vasculitis includes but is not limited to Behçet's syndrome, Churg-Strauss syndrome, cutaneous vasculitis, Henoch-Schönlein purpura, Microscopic polyangiitis, Wegener's granulomatosis, cryoglobulinemic vasculitis, hypersensitivity vasculitis, vasculitis secondary to connective tissue disorders, and vasculitis secondary to viral infections.

The later type of vasculitis, associated with viral infections, is commonly seen with hepatitis B and C viruses, but may also be seen with HIV, Ebstein-Barr virus, cytomegovirus and Parvovirus B-19. More recently, the presence or absence of an antineutrophil cytoplasmic antibody (ANCA) has refined the classification.

Medium vessel vasculitis includes but is not limited to Thromboangiitis obliterans (small and medium vessel), Cutaneous vasculitis (small and medium vessel), Kawasaki disease, Polyarteritis nodosa (small and medium vessel), and primary central nervous system vasculitis.

Large vessel vasculitis includes but is not limited to Polymyalgia rheumatica, Takayasu's arteritis, Temporal (giant cell) arteritis.

Without being bound to a particularly theory, levocetirizine and montelukast work to block the H1 and leukotriene receptors, respectively. Thus, levocetirizine and montelukast effectively block the release of histamine to reduce systemic swelling/edema and improve lung function by inhibiting the release of leukotrienes. However, it is the combination of levocetirizine and montelukast, approximately 70 years newer than the prototype antihistamine, diphenhydramine that is scientifically more effective than its predecessor in reducing inflammation. Levocetirzine blocks the acute phase response to injury not only as an antihistamine but through its anti-inflammatory properties which include in part, the suppression of Interleukin 6 (IL-6) and Interleukin 8 (IL-8). IL-6 is one of the most important mediators of both the acute phase reaction to injury and fever.

Moreover, levocetirizine blocks IL-8, the signaling protein responsible for chemotaxis in target cells, primarily neutrophils, causing them to migrate to the site of injury/inflammation. In addition to neutrophils there are a wide range of other cells, e.g., endothelial cells, mast cells, macrophages, and keritinocytes that respond to IL-8 as well.

Montelukast blocks the actions of leukotriene $D_4$ at the receptor. Leukotriene $D_4$ is most potent of the cysteinyl leukotrienes in contracting airway smooth muscle. It promotes the recruitment of eosinophils, dendritic cells (antigen presenting cells) and T cells, which in turn in increases cell recruitment and activation. Clinically, montelukast has been shown to increase FEV1 by 15% in minutes to hours following administration.

Both levocetirizine and montelukast decrease eosinophil quantity/migration. Eosinophil infiltration is considered by some authorities as a hallmark of inflammation. Both molecules block the acute and late phase responses to inflammation. With continuous dosing, if the acute phase is blocked, the late phase becomes less of an issue, whereas T-cell memory dissipates with time. Given the multiple sites of action within the inflammatory pathway underscored by the safety of the molecules, a unique synergy can be identified between levocetirizine and montelukast. This synergy is effective in treating many forms of vasculitis.

Administration of levocetirizine and montelukast in combination exhibits unexpectedly superior results in the treatment of vasculitis. Moreover, combinations of levocetirizine and montelukast can be safely used in conjunction with many existing treatment protocols. Both are Pregnancy Category B medications and both are FDA approved in the United States for treatment of other disease states down to six months of age. For example, antibiotics such as amoxicillin/beta clavulanic acid (Augmentin®) can be administered to a patient in combination with levocetirizine and montelukast. As another example, glucocorticoids, including but not limited to prednisone, may also be administered to a patient treated with a combination of levocetirizine and montelukast. Additionally, cytotoxic and immunosuppressant agents such as cyclophosphamide, azothiaprine, methotrexate, mycofenolate mofetil, omalizumab (Xolair®), rituximab, interferon alpha and anti-IL 5 antibodies can used in combination with levocetirizine and montelukast. The combination of levocetirizine and montelukast may be administered as a short-term therapy or as a long-term therapy.

Given the intrinsic safety of both levocetirizine and montelukast, in some embodiments, the combination may be used with almost any of the aforementioned agents. Therapy may be primary or secondary, and if secondary, administered to supplement existing treatment to effect the desired response. Once achieved, (reduction in symptoms/improvement in associated laboratory values) the more toxic, former therapy (or therapies) may be tapered and in select cases, completely discontinued. The combination of levocetirizine plus montelukast may continue until the defined laboratory or clinical endpoint (s) traditionally acknowledged in the literature for that specific type of vasculitis has (have) been reached.

As will be readily apparent to one skilled in the art, the useful in vivo dosage of levocetirizine and montelukast to be administered and the particular mode of administration will vary depending upon the age, weight, medical condition of the patient, the severity of the condition to be treated, the route of administration, the renal and hepatic function of the patient, and mammalian species treated, the particular compounds employed, and the specific use for which these compounds are employed. The determination of effective dosage levels, that is the dosage levels necessary to achieve the desired result, can be accomplished by one skilled in the art using routine pharmacological methods. Typically, human clinical applications of products are commenced at lower dosage levels, with dosage level being increased until the desired effect is achieved. Advantageously, compounds of the present embodiments may be administered, for example, in a single daily dose, or the total daily dosage may be administered in divided doses of two, three or four times daily.

Depending upon the nature and extent of the particular type of vaculitis, daily or twice daily dosing may be required to suppress inflammation. A non-limiting example lies in the treatment of Temporal arteritis.

Temporal arteritis or giant cell arteritis is an inflammatory disorder of the large and medium arteries of the head. Common symptoms include in part, fever, headache, reduced visual acuity, scalp tenderness, and tinnitus. Traditional treatment involves the use of glucocorticoids such as prednisone in relatively high doses: 40-60 mg/ day for extended periods of time, i.e., months to years. The prolonged use of steroids is associated with a myriad of side effects listed in Table III. Thus, a non-limiting example of treating temporal arteritis with a combination of levocetirizine and montelukast can be accomplished as summarized in Table VII.

TABLE VII

DOSING OF LEVOCETIRIZINE AND MONTELUKAST FOR THE TREATMENT OF VASCULITIS - TEMPORAL ARTERITIS AS A CLASSIC EXAMPLE

| | |
|---|---|
| Levocetirizine | 5-15 mg total dose/day administered daily or twice daily as a divided dose |
| Montelukast | 10-20 mg total dose/day administered daily or twice daily as a divided dose |
| Duration | 6-18 months |
| Laboratory target | Sedimentation rate of less than 20 mm/hr |
| Mean Sedimentation rate at the time of diagnosis (sedimentation rate is a non-specific index of inflammation) | 45-55 mm/hr |

Several embodiments relate to the use of a combination of levocetirizine and montelukast for the treatment of Churg-Strauss Syndrome. Churg-Strauss Syndrome is a non-inheritable and nontransmissible vasculitis of the medium and small vessels leading to necrosis. It is a multisystem disorder characterized by chronic rhinosinusitis, asthma and peripheral eosinophilia. Vasculitis is usually not apparent in the initial stages of the disease. Asthma is the cardinal feature and is present in 90% of cases. Otolaryngology signs and symptoms such as rhinosinusitis, nasal polyposis, and serous otitis media are found in approximately 50% of patients. Cardiovascular manifestations account for half the deaths; peripheral neuropathy, usually mononeuitis multiplex, is found in 75% of cases. Other commonly involved organ systems are the skin, gastrointestinal tract and kidneys.

The primary therapy for Churg-Strauss Syndrome are the systemic glucocorticoids. Cytotoxic or immunosuppressive agents (cyclophosphamide, azothiaprine, methotrexate, etc.) are added in those patients with advanced disease or those who fail to respond to the steroids. Several cases have reported improvement in patients with refractory disease following the addition of high dose IV gamma globulin. Anti-IgE therapy (Xolair®, omalizumab), mycofenolate mofetil, hydrourea, rituximab, interferon alpha and anti-IL 5 antibodies have likewise been tried with various degrees of success. Most agents are wrought with a constellation of side effects which preclude their long-term use.

One controversial area of treatment of Churg-Strauss Syndrome lies in the use of the leukotriene modulators. Churg-Strauss was reported as a rare complication in patients with glucocorticoid dependent asthma also treated with a leukotriene modifying agent, e.g., zafirlukast, montelukast, pranlukast, or zileuton, and usually in the setting of glucocorticoid reduction. Without being bound to a particularly theory, it is believed in these cases, the leukotriene was insufficient to control the Syndrome. Separately, it is possible that glucocorticoid withdrawal facilitated by leukotriene therapy led to the manifestation of the disease process itself.

However, these theories and the reported complication of montelukast precipitating Churg-Strauss Syndrome are overcome by the combined use of levocetirizine plus montelukast which act synergistically, in part, to decrease eosinophil quantity and/or migration. Example 1 is a case study of a 78 year old male with Churg-Strauss Syndrome successfully treated with a combination of levocetirizine and montelukast.

Some embodiments also relate to the use of the combination of levocetirizine and montelukast for the treatment of Henoch Schonlein Purpura (HSP). HSP is a systemic vasculitis of unknown etiology commonly found in children. The classic triad of symptoms includes purpura (small hemorrhages in the skin), arthritis, and abdominal pain. The disease usually follows an infection such as pharyngitis. Patients characteristically present with purpura on the legs and buttocks, joint pain involving the knees, ankles and elbows, and abdominal pain accompanied by nausea, vomiting, diarrhea or constipation.

Deposition of immune complexes containing IgA can lead to kidney disease in 40% of patients. Although HSP itself is considering self-limiting, approximately 1% of patients develop chronic kidney disease with associated hypertension.

Medical therapy has traditionally consisted of the anti-inflammatory medications: antihistamines and the non-steroidal inflammatory agents. More refractory cases are treated with steroids, particularly in the 33% of cases that reoccur.

HSP and its symptoms, including recurrent HSP that is poorly responsive to other therapeutic agents such as ibuprofen and diphenhydramine, can be effectively treated with the remarkably safe and synergistic combination of levocetirizine and montelukast. Example 2 is a case study of a 9 year old male with HSP successfully treated with a combination of levocetirizine and montelukast.

Definitions

The term "effective amount" includes an amount effective, at dosages and for periods of time necessary, to achieve the desired result, e.g., sufficient to treat vasculitis in a patient or subject. An effective amount of levocetirizine and montelukast may vary according to factors such as the disease state, age, and weight of the subject, and the ability of levocetirizine and montelukast to elicit a desired response in the subject. Dosage regimens may be adjusted to provide the optimum therapeutic response. An effective amount is also one in which any toxic or detrimental effects (e.g., side effects) of levocetirizine and montelukast are outweighed by the therapeutically beneficial effects.

"Ameliorate," "amelioration," "improvement" or the like refers to, for example, a detectable improvement or a detectable change consistent with improvement that occurs in a subject or in at least a minority of subjects, e.g., in at least about 2%, 5%, 10%, 15%, 20%, 25%, 30%, 40%, 50%, 60%, 70%, 75%, 80%, 85%, 90%, 95%, 98%, 100% or in a range between any two of these values. Such improvement or change may be observed in treated subjects as compared to subjects not treated with levocetirizine and montelukast, where the untreated subjects have, or are subject to developing, the same or similar disease, condition, symptom or the like. Amelioration of a disease, condition, symptom or assay parameter may be determined subjectively or objectively, e.g., self-assessment by a subject(s), by a clinician's assessment or by conducting an appropriate assay or measurement, including, e.g., a quality of life assessment, a slowed progression of a disease(s) or condition(s), a reduced severity of a disease(s) or condition(s), or a suitable assay(s) for the level or activity(ies) of a biomolecule(s), cell(s), by detection of respiratory or inflammatory disorders in a subject, and/or by modalities such as, but not limited to photographs, video, digital imaging and pulmonary function tests. Amelioration may be transient, prolonged or permanent or it may be variable at relevant times during or after levocetirizine and montelukast are administered to a subject or is used in an assay or other method described herein or a cited reference, e.g., within timeframes described infra, or about 1 hour after the administration or use of levocetirizine and montelukast to about 28 days, or 1, 3, 6, 9 months or more after a subject(s) has received such treatment.

The "modulation" of, e.g., a symptom, level or biological activity of a molecule, or the like, refers, for example, to the symptom or activity, or the like that is detectably increased or decreased. Such increase or decrease may be observed in treated subjects as compared to subjects not treated with levocetirizine and montelukast, where the untreated subjects have, or are subject to developing, the same or similar disease, condition, symptom or the like. Such increases or decreases may be at least about 2%, 5%, 10%, 15%, 20%, 25%, 30%, 40%, 50%, 60%, 70%, 75%, 80%, 85%, 90%, 95%, 98%, 100%, 150%, 200%, 250%, 300%, 400%, 500%, 1000% or more or within any range between any two of these values. Modulation may be determined subjectively or objectively, e.g., by the subject's self assessment, by a clinician's assessment or by conducting an appropriate assay or measurement, including, e.g., quality of life assessments, suitable assays for the level or activity of molecules, cells or cell migration within a subject and/or by modalities such as, but not limited to photographs, video, digital imaging and pulmonary function tests. Modulation may be transient, prolonged or permanent or it may be variable at relevant times during or after levocetirizine and montelukast are administered to a subject or is used in an assay or other method described herein or a cited reference, e.g., within times described infra, or about 1 hour after the administration or use of levocetirizine and montelukast to about 3, 6, 9 months or more after a subject(s) has received levocetirizine and montelukast.

As used herein, the terms "prevent," "preventing," and "prevention" refer to the prevention of the recurrence, onset, or development of vasculitis. Preventing includes protecting against the occurrence and severity of upper and/or lower respiratory tract infections.

As used herein, the term "prophylactically effective amount" refers to the amount of a therapy (e.g., a pharmaceutical composition comprising montelukast and levocetirizine) which is sufficient to result in the prevention of the development, recurrence, or onset of vasculitis or to enhance or improve the prophylactic effect(s) of another therapy.

As used herein, "subject" includes organisms which are capable of suffering from vasculitis or other disorder treatable by a combination of montelukast and levocetirizine or who could otherwise benefit from the administration of montelukast and levocetirizine as described herein, such as human and non-human animals. Preferred human animals include human subjects. The term "non-human animals" includes all vertebrates, e.g., mammals, e.g., rodents, e.g., mice, and non-mammals, such as non-human primates, e.g., sheep, dog, cow, chickens, amphibians, reptiles, etc.

The following Examples are presented for the purposes of illustration and should not be construed as limitations.

EXAMPLES

Example 1

Case Study: 78-year-old male with Churg-Strauss Syndrome (eosinophilic vasculitis)

| Patient: | TC |
|---|---|
| DOB: | May 12, 1934 |
| Age: | 78 |

The patient is a 78-year-old male seen and evaluated in the office in Mar. 20, 2012 for chronic rhinosinusitis and allergic rhinitis dating back for decades. For four to five years he had been also treated for asthma. Symptoms included cough, congestion, postnasal drainage, wheezing and intermittent hoarseness. At the time of the initial visit he was completing a two-week course of azithromycin, a second-generation macrolide antibiotic.

Occupational History: Public Health Professor/attorney
Major Medical Problems:
Asthma
Allergic rhinitis
Chronic rhinosinusitis
Elevated eosinophil counts
Severe heart disease with an ejection fraction of 36% on presentation (normal: 55-75%).
Significantly elevated total serum IgE: 439 IU/dl (normal <158 IU/ml)
Unsuccessful trial of Xolair® (omalizumab) 2010 for severe asthma/mechanism-monoclonal antibody that binds to mast cells and basophils, thereby decreasing mediator release. Serious reactions include anaphylaxis, malignancy, severe thrombocytopenia (low platelet count) and severe injection site reactions
Surgery:
Undescended testicle—age 2
Appendectomy—age 8
Tonsillectomy as a child
Sinus surgery—Dec. 18, 2009 underscored by the use of steroids 5× within the preceding 12-month period
Habits:
Coffee—2-3 cups/day
Alcohol—1-2 glasses of wine/day
Tobacco use—smoked a pipe while in college Medications on Presentation:
Advair 500/50® twice a day (fluticasone/salmeterol inhaler, i.e., an inhaled steroid with a long-acting bronchodilator. The product comes in three strengths 100/50, 250/50 and 500/50.)
Spiriva® (tiptropium)—once a day (inhaled anticholinergic to produce bronchodilation)
Nasonex® (mometasone) nasal steroid spray—two squirts each nostril daily
prednisone—20 mg twice a day
azithromycin 250 mg per day/completing course of therapy (second generation macrolide antibiotic)
carvedilol 6.25 mg orally twice a day (beta blocker)
lisinopril 2.5 mg twice a day (ACE inhibitor)
omeprazole 20 mg twice a day (proton pump inhibitor used at double the usual dose as prophylaxis for the prevention of gastric ulcers while the patient is on steroids)
spironolactone 25 mg, 1.5 per day (potassium sparing diuretic)
Flomax® (tamsulosin) 0.4 mg once a day (peripherally acting alpha blocker to improve urine flow)
Zyrtec® (cetirizine) 10 mg once a day (second generation sedating antihistamine with half the receptor affinity and twice the sedation profile of the pure isomer, levocetirizine)

Pertinent Physical Examination:
Weight: 160#/72.7 kg
Height: 5'7"/170 cm
HEENT:

| Ears | 10x micro/gray tympanic membranes, mild tympanosclerosis, no middle ear effusion |
|---|---|
| Nose | right inferior septal spur, high moisture content - 2.75+/4+ |
| Throat | post nasal drainage, otherwise normal oropharynx |
| Neck | without adenopathy |

From the Cardiology Evaluation Mar. 29, 2012:
Vital signs: B/P 104/56 sitting and 104/50 standing—left arm; heart rate 60 beats/minute and regular
Laboratory Data:
Historical Eosinophil Levels

| Feb. 9, 2010 | 40.7% markedly elevated (normal approximately 1-5% of all white blood cells) requiring hospitalization at Scripps Green Hospital from Feb. 9, 2012 through Feb. 16, 2010 |
|---|---|
| Feb. 16, 2012 | 0.6% |
| Apr. 21, 2010 | 2.0% |
| Jun. 16, 2010 | 7.7% elevated |
| Dec. 19, 2010 | 7.9% elevated |
| Jul. 28, 2011 | 4.0% |
| Dec. 19, 2011 | 6.3% elevated |
| Feb. 24, 2012 | 15.0% significantly elevated - 1.0 K/µL |

Eosinophil Count

| Feb. 24, 2012 | 1.0 K/µL significantly elevated - 15% of all white cell (normal 0.0-0.4 K/µL) |
|---|---|
| Mar. 20, 2012 | 0.1 K/µL or 1% of all white cells |
| Apr. 9, 2012 | 0.0 K/µL |
| Apr. 20, 2012 | 0.1 K/µL |
| Jul. 16, 2012 | 0.3 K/µL |
| Oct. 15, 2012 | 0.3 K/µL |

B-Type natriuretic peptide (BNP)

| | |
|---|---|
| Feb. 24, 2012 | 121 pg/ml elevated (normal 0-100 pg/ml) |
| Mar. 20, 2012 | 140 pg/ml elevated |
| Apr. 9, 2012 | 70 pg/ml |
| Apr. 20, 2012 | 88 pg/ml |
| Jul. 16, 2012 | 74 pg/ml |

The B-type natriuretic peptide is a 32 amino acid peptide secreted by the heart ventricles during periods of stress. Given a half-life of 20 minutes, its utility is ruling out an acute cardiac event to a sensitivity of 90% when the value is less than 100.

In the present case the B-Type natriuretic peptide was elevated prior to the refined treatment protocol initiated on Mar. 20, 2012. The elevation was present despite the use of steroids and the antihistamine, cetirizine.

IgE (Immunoglobulin E)

| | |
|---|---|
| February 2010 | 771 IU/ml markedly elevated (normal <158 IU/ml) measured during the Scripps Green Hospitalization; diagnosis of Churg-Strauss Syndrome |
| Mar. 7, 2012 | 439 IU/ml significantly elevated (normal <158 IU/ml) |
| Apr. 9, 2012 | 332 IU/ml |
| Jul. 16, 2012 | 223 IU/ml |
| Oct. 15, 2012 | 281 IU/ml |

Basic blood count and chemistries—normal

Mar. 20, 2102

WBC: 10000/μL, hemoglobin 14.2 g/dL, hematocrit 41.6%, platelet count 246, 000/μL, Sodium 139 mEq/L, potassium 4.2 mEq/L, chloride 103 mEq/L, bicarbonate 32 mEq/L, BUN 21 mg/dL, creatinine 0.85 mg/dL Jul. 16, 2012

WBC: 7300/μL, hemoglobin 13.6 g/dL, hematocrit 39.3%, platelet count 191,000/μL, Sodium 139 mEq/L, potassium 4.8 mEq/L, chloride 104 mEq/L, bicarbonate 31 mEq/L, BUN 21 mg/dL, creatinine 1.02 mg/dL, alkaline phosphatase 39 U/L, ALT 21 U/L, AST 31 U/L, total protein 6.4 g/dL, albumin 3.9 g/dL, globulin 2.5 g/dL Imaging:

CT Scans of the Sinuses:

Mar. 8, 2012—significant mucosal thickening in the left maxillary, frontal and ethmoid sinuses Apr. 9, 2012—almost complete clearing of the previously documented pathology reflecting in part, the combined use of levocetirizine and montelukast Bicycle Exercise Echo Stress Test:

Feb. 28, 2012: LVEF (left ventricular ejection fraction) 36% by true volume technique (normal: 55-75%). Normal RVEF (right ventricular ejection fraction). Elevated pulmonary artery systolic pressure 41 mm Hg/mean of approximately 27 mm Hg. Pulmonary hypertension is present when the mean exceeds 25 mm Hg at rest.

The ejection fraction is the percentage of blood pumped out the heart (ventricle) with each beat. The normal range is 55-75%. Echo volumetric measurement of the performance of the left and right ventricles is used worldwide as the ratio of dimensions between the ventricles in systole and diastole.

Jul. 17, 2012: The left ventricular ejection fraction improved to 58% from 36% compared with Feb. 28, 2012 by the true volume technique. Left ventricular diastolic diameter improved from 7.4 cm to 6.8 cm. (normal: <5.7 cm). Systolic pulmonary artery pressure improved to 36 mm Hg or an approximate mean of 23.6 mm Hg overall reflecting a remarkable improvement in cardiac output and resolution of the pulmonary hypertension Assessment: 78 year old male with Churg-Strauss Syndrome/associated severe heart and lung disease.

Treatment Regimen: initiated Mar. 20, 2012

Stop Zyrtec® (cetirizine) 10 mg daily and replace with the pure isomer, levocetirizine 5 mg orally per day.

Add montelukast 10 mg orally per day.

The nature of the products, safety, pathway and science were discussed in detail. The goal was to improve cardiopulmonary function.

Clinical Course:

The patient was thereafter seen in follow-up Apr. 23, 2012. Over the prior month there had been a dramatic improvement in symptoms with decreased cough, congestion and post-nasal drainage. In addition were stable eosinophil counts and improved lung peak expiratory flow measurements. Recent peak expiratory flow data recorded in liters/minute had been as high as 450-470 L/min, contrasted to ~380 L/min on Jan. 29, 2012. Moreover, prednisone which had been between 10-40 mg/day since February 2012, had been tapered to 5 mg/day after two and one half weeks on the new treatment protocol. The prednisone was subsequently lowered over the summer to 2.5 mg every other day and completely discontinued at the end of September 2012.

Figure 2:
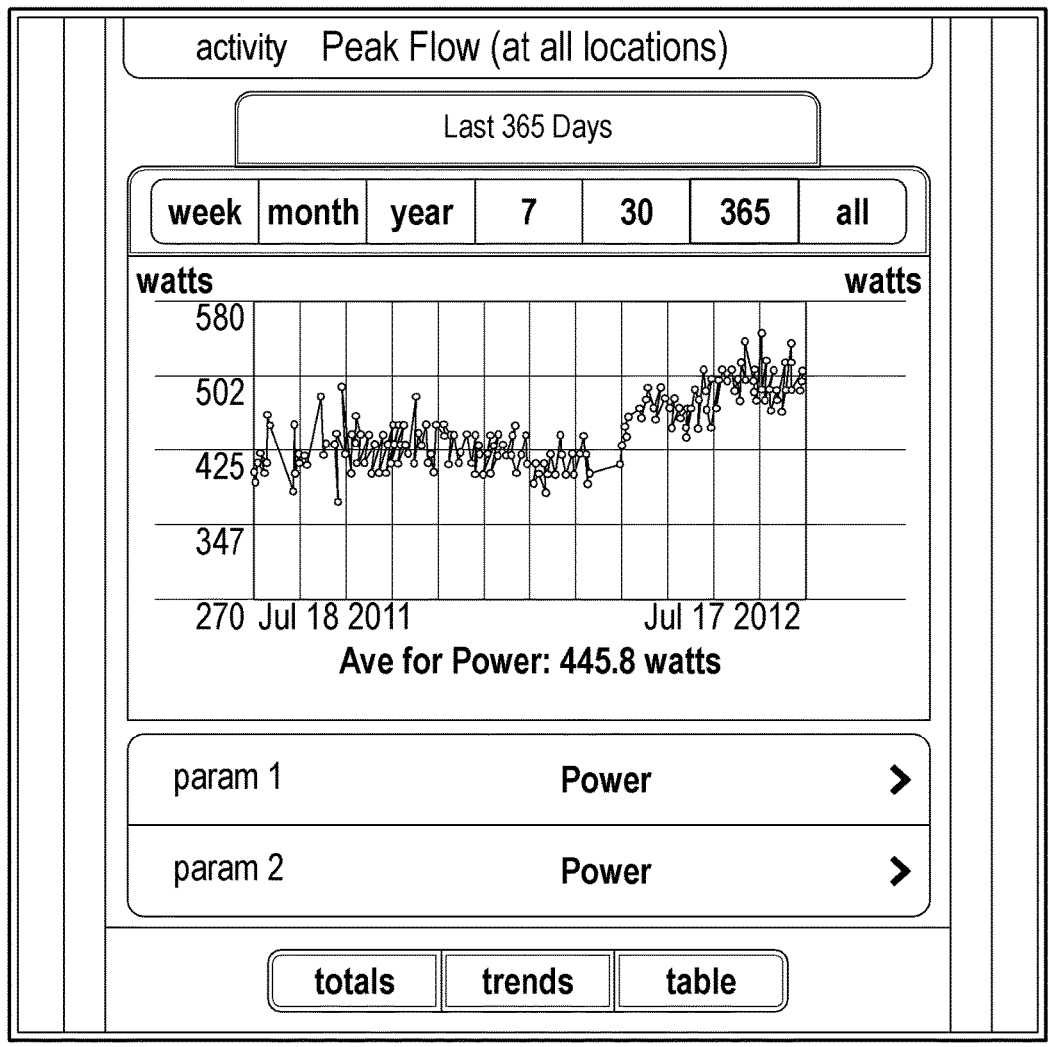
FIG. 2 is a diagram showing one year of peak expiratory flow data (L/min) from July 2011 through July 2012 of a patient with Churg-Strauss Syndrome responding to the combination of levocetirizine and montelukast treatment as described in Example 1.

On Jul. 17, 2012 the patient bought in a year of peak flow data graphically depicting his four month response to the combined medications: levocetirizine plus montelukast. His peak expiratory flows were, "the highest levels ever" at 490-500 L/min. Normal for age and height is 465 L/min. The peak expiratory flow data from July 2011 to July 2012 are depicted in FIG. 2. The graph demonstrates the remarkable response to the combination of levocetirizine and montelukast initiated on Mar. 20, 2012.

Independent Cardiology Assessment Jul. 17, 2012:

An independent cardiology evaluation four months following initiation of the refined treatment protocol, levocetirizine plus montelukast, documented a significantly improved cardiac output as well as resolution of the patient's pulmonary hypertension. The repeat echocardiogram Jul. 17, 2012 when compared to Feb. 28, 2012 detailed improvement in the left ventricular ejection fraction from 36% to 58% (normal 55-75%). The left ventricular diastolic diameter had improved to 6.8 cm; systolic pulmonary artery pressure had improved to a normal 36 mm Hg.

Overview:

This case is a clinical example of the remarkable anti-inflammatory synergy between two extremely safe molecules: levocetirizine plus montelukast for the treatment of one form of vasculitis, Churg-Strauss Syndrome. The combination therapy has dramatically improved quality of life by eliminating the daily use of steroids and restoring cardiopulmonary function. Objective data includes serial peak expiratory flow measurements, serum BNP (B-Type natriuretic peptide) testing and serial echocardiograms.

Example 2

Case Study: 9-year-old male with Henoch Schonlein Purpura

| | |
|---|---|
| Patient | ZH |
| DOB | Jun. 25, 2002 |
| Age | 9 |

The patient is a 9-year-old male originally seen and evaluated in London, England, Feb. 16, 2012-Feb. 18, 2012, for Henoch Schonlein Purpura (HSP) heralded by a rash on the posterior aspect of his legs and difficulty walking. Following an overnight stay at Royal Free Hospital, ZH was discharged to his parents on ibuprofen, 160 mg orally, three times a day for one week. A second episode of purpura and arthritis occurred on Mar. 14, 2012 underscored by an apparent upper respiratory tract infection for which he was given cefdinir by a local allergist. The third episode began Mar. 23, 2012 during a trip to Mammoth Lakes, Calif. Documented was swelling of the left hand, left foot and penis. Treatment consisted of ibuprofen, 300 mg orally, twice a day and diphenhydramine. He was thereafter seen in our office on Apr. 2, 2012 and placed on a ninety-day trial of levocetirizine 2.5 mg orally at night and montelukast 5 mg orally at night. The ibuprofen and diphenhydramine were discontinued.

ZH returned for follow-up on May 3, 2012 with a sore throat and fever. With respect to the pre-infection HSP, there had been no resurgence of swelling, purpura or joint pain. The patient was cultured and placed on amoxicillin/beta clavulanic acid (Augmentin®) 600 mg orally, twice a day for 10 days. The culture grew Group A beta-hemolytic strep. A mild exacerbation of purpura and swelling occurring the next day, May 4, 2012, which responded within 24 hours by temporarily increasing the dose of levocetirizine and montelukast to twice a day. Long-term therapy was discontinued at the end of August 2012 with no interval exacerbation of the disease process.

Physical examination: initial visit Apr. 2, 2012
Vital signs: Temperature—afebrile
Weight 76#/34.5 k
HEENT:

| Ears | AS (left): gray tympanic membrane |
| --- | --- |
| | AD (right): gray tympanic membrane |
| | No infection |
| Nose | 2+ moisture content, no anterior lesions seen |
| Nasopharynx | significant shelf of adenoid tissue superiorly (photographed) |
| Throat | s/p tonsillectomy |
| Larynx | left vocal cord nodule |
| Neck | without adenopathy |
| Extremities | mild swelling of the left forearm (photographed) |

Physical examination: follow-up visit May 3, 2012
Temperature 99° F. tympanic
Weight 76#/34.5 kg
HEENT:

| Ears (10x micro) | AS (left): serous middle ear effusion, mild erythema |
| --- | --- |
| | AD (right): gray tympanic membrane |
| Nose | 2.75+/4+ moisture content, 2+ erythema |
| Throat | s/p tonsillectomy, cultured pharynx |
| Neck | right jugulodigastric node palpable |
| Extremities | no purpura or swelling at this visit |

Medications (Apr. 2, 2012): ibuprofen 300 mg 2× per day for the preceding two weeks, supplemental diphenhydramine (Benadryl®) 25 mg, as needed, Cromolyn (Nasal-Crom®) for allergies, as needed, cefdinir 250 mg/5 cc—one teaspoon orally, twice a day ending Mar. 24, 2012

Surgical history: tympanostomy tubes age 2, tonsillectomy and adenoidectomy age 4, pin—left arm June 2011, revision adenoidectomy May 23, 2012

Major medical problems: none
Social History: 4$^{th}$ grade student
Allergies to Medication: none Laboratory Data:
May 19, 2012
CBC: white count 4.3 K/μL, hemoglobin 13.2 g/dL, hematocrit 38.5%, platelet count 245,000/μL
Renal panel: Sodium 141 mEq/L, potassium 4.6 mEq/L, chloride 107 mEq/L, bicarbonate 29 mEq/L, BUN 14 mg/dL, creatinine 0.55 mg/dL, glucose 74.
Comprehensive metabolic panel—normal.
Urinalysis: no blood or protein
May 23, 2012
T and B cell panel:
Normal except for natural killer cells—426 cells/uL (normal 74-254 cells/uL)
NK cells: 21% elevated (normal 4-14%)
IgG1 581 mg/dL
IgG2 326 mg/dL
IgG3 44.1mg/dL
IgG4 76.9 mg/dL
Total IgG 1003 mg/dL (normal 598-1379 mg/dL)
IgA 154 mg/dL (normal 33-258 mg/dL)
IgE 11 IU/ml (normal 0-60 IU/ml)
IgM 67 mg/dL (normal 47-200 mg/dL)
Assessment: recurrent Henoch Schonlein Purpura
Treatment Regimen:
Levocetirizine 2.5 mg orally at night×90 days
Montelukast 5 mg orally at night×90 days
Doses safely increased to bid×10 days during the antibiotic treatment for a confirmed Group A strep infection May 2012.

Overview:

This case is an example of the remarkable anti-inflammatory synergy between two extremely safe molecules: levocetirizine plus montelukast for the treatment of recurrent Henoch Schonlein Purpura (HSP) poorly responsive to ibuprofen and diphenhydramine (Benadryl®). There were no complications from daily and twice daily dosing.

What is claimed is:

1. A method of treating vasculitis in a patient in need thereof comprising administering to the patient an effective amount of a combination of levocetirizine and montelukast, wherein vasculitis comprises Henoch Schonlein Purpura.

2. The method of claim 1, wherein the combination is administered in a sequential manner.

3. The method of claim 1, wherein the combination is administered in a substantially simultaneous manner.

4. The method of claim 1, wherein the combination is administered at the onset of symptoms.

5. The method of claim 1, wherein the combination is administered to the patient by one or more of the routes consisting of enteral, intravenous, intraperitoneal, inhalation, intramuscular, subcutaneous and oral.

6. The method of claim 5, wherein the levocetirizine and montelukast are administered by the same route.

7. The method of claim 1, wherein the combination is administered at the onset of symptoms.

8. The method of claim 1, further comprising the administration of an active agent.

9. The method of claim 8, wherein the active agent is a glucocorticoid.

10. The method of claim 8, wherein the active agent is a steroidal anti-inflammatory agent.

11. The method of claim 8, wherein the active agent is a non-steroidal anti-inflammatory agent.

12. The method of claim 8, wherein the active agent is an antihistamine.

13. The method of claim 8, wherein the active agent is a cytotoxic drug.

14. The method of claim 8, wherein the active agent is an immunosuppressive agent.

15. The method of claim 8, wherein the active agent is a monoclonal antibody.

* * * * *